(12) United States Patent
Putnam et al.

(10) Patent No.: US 7,409,354 B2
(45) Date of Patent: Aug. 5, 2008

(54) METHOD AND APPARATUS FOR OPERATIVE EVENT DOCUMENTATION AND RELATED DATA MANAGEMENT

(75) Inventors: Matt D. Putnam, Edina, MN (US); Mark G. Smith, Edina, MN (US)

(73) Assignee: mEdison Online Inc., Edina, MN (US)

( * ) Notice: Subject to any disclaimer, the term of this patent is extended or adjusted under 35 U.S.C. 154(b) by 1061 days.

(21) Appl. No.: 10/134,319

(22) Filed: Apr. 29, 2002

(65) Prior Publication Data

US 2003/0101081 A1    May 29, 2003

Related U.S. Application Data

(60) Provisional application No. 60/334,194, filed on Nov. 29, 2001.

(51) Int. Cl.
*G06Q 50/00* (2006.01)
(52) U.S. Cl. .............................. 705/2; 705/3
(58) Field of Classification Search .............. 705/2, 705/3; 600/300
See application file for complete search history.

(56) References Cited

U.S. PATENT DOCUMENTS

| | | | |
|---|---|---|---|
| 5,301,105 A | | 4/1994 | Cummings et al. |
| 5,307,262 A | * | 4/1994 | Ertel ............................. 705/2 |
| 5,483,443 A | * | 1/1996 | Milstein et al. ................. 705/3 |
| 5,664,109 A | * | 9/1997 | Johnson et al. ................. 705/2 |
| 5,835,897 A | | 11/1998 | Dang |
| 6,014,630 A | * | 1/2000 | Jeacock et al. ................. 705/3 |
| 6,088,677 A | | 7/2000 | Spurgeon |
| 6,151,581 A | * | 11/2000 | Kraftson et al. ................ 705/3 |
| 6,177,940 B1 | * | 1/2001 | Bond et al. .................. 434/262 |
| 6,182,047 B1 | * | 1/2001 | Dirbas ............................ 705/3 |
| 6,450,956 B1 | * | 9/2002 | Rappaport et al. ........... 600/300 |
| 6,684,276 B2 | * | 1/2004 | Walker et al. .................. 710/73 |
| 2002/0032580 A1 | * | 3/2002 | Hopkins ......................... 705/2 |
| 2002/0069085 A1 | * | 6/2002 | Engel et al. .................... 705/2 |
| 2002/0082480 A1 | * | 6/2002 | Riff et al. .................... 600/300 |
| 2002/0138155 A1 | * | 9/2002 | Bristol .......................... 700/2 |
| 2002/0147615 A1 | * | 10/2002 | Doerr et al. .................... 705/2 |
| 2003/0033169 A1 | * | 2/2003 | Dew .............................. 705/3 |

OTHER PUBLICATIONS

Bell Atlantic and EMX Team Up to Provide Doctors Instant Online Access to Medical Data, PR Newswire, Feb. 23, 1999.*

* cited by examiner

*Primary Examiner*—C. Luke Giligan
*Assistant Examiner*—Lena Najarian
(74) *Attorney, Agent, or Firm*—Schwegman, Lundberg & Woessner, P.A.

(57) ABSTRACT

In one embodiment, method and apparatus are disclosed which provide that a plurality of physicians each enter operative event data into an operative event database, wherein the operative event data documents planned or completed operative events and the physicians enter the operative event data use a wide area network through a user interface assisting the physicians in coding operative events in a consistent manner. The physicians access the operative event database to obtain information concerning upcoming or previously performed operative events, with a service provider maintaining an on-line system including one or more servers to support the entering of operative event data into the database through the Internet and the user interface. The physicians subscribe to the on-line system wherein the physicians are allowed access and use the on-line system, and wherein the physicians retain control over the use and disposition of the operative event data entered by the physician.

56 Claims, 25 Drawing Sheets

Next Step                                                                   Page 1 of 1

Logout                    mEdison Online                    About

Patient: BARBARA B. SMITH
Select Next Step

[Pick CPT]  [Short Form Exam]

───────────────────────────────────────────────

[Main Menu]  [Back]

A confidential mEdisonOnline transaction for Doc M. Test, MD
                              contact by email https://www.medisononline.net/4DACTION/LoopPost                    11/19/2001

Fig.15A

Select CPT Step One                                              Page 1 of 1

Logout                mEdison Online           About

Select Category

BARBARA B SMITH
Right Forearm and Wrist

- Arthroscopy
- Casts
- General
- Integrument
- Nerve
- Vascular

A confidential mEdisonOnline transaction for Doc M. Test, MD
contact by email

.../PickCPTMenu~Skel?side=Right&loc=Forearm_and_Wrist&pwkey=000001U&patientkey11/19/2001

Fig.15C

Select CPT Step One                                          Page 1 of 1

Logout          mEdison Online          About
BARBARA B SMITH
Right Forearm and Wrist
Nerve

Select SubCategory 1
- Excision
- Neuroplasty
- NeuroStim
- Repair

A confidential mEdisonOnline transaction for Doc M. Test, MD
contact by email https://www.medisononline.net/4DACTION/PickCPTMenu/Step1        11/19/2001

Fig.15D

Select CPT Step 3                                         Page 1 of 1

Logout           mEdison Online          About

BARBARA B SMITH
Right Forearm and Wrist
Nerve

Select SubCategory 2

64719
64721 Neuroplasty and/or transposition

A confidential mEdisonOnline transaction for Doc M. Test, MD
contact by email https://www.medisononline.net/4DACTION/PickCPTMenu/Step1    11/19/2001

Fig.15E

Create New Event                                                                 Page 1 of 1

Logout                 mEdison Online                 About

Enter event information

| Patient Key | 000009Z | Patient Name | BARBARA B SMITH |
|---|---|---|---|
| Gender | 9 | DOB | 03/12/1945 |
| SSN | 560683734 | Side | Left |
| CPT | 64721 Neuroplasty and/or transposition: wrist median nerve at carpal tunnel | | |

| | |
|---|---|
| Hospital | Fairview-University Medical Center |
| Event Date | 11/19/2001 |
| Med Record Number | |
| Incision Start | Start Time: _____ OR<br>Select Hour: 00  Select Minutes: 00 |
| Incision Close | Stop Time: _____ OR<br>Select Hour: 00  Select Minutes: 00 |
| Referring Physician(s) | None   None |
| Assistant(s) | None   None |
| Asst Proficiency Level(s) | Assistant 1: ____  Assistant 2: ____ |

| ICD9 | Description | PreOp | PostOp |
|---|---|---|---|
| 354 | Median neuropathy at Carpal Tunnel | PreOp ☑ | PostOp ☑ |
| 714 | Rheumatoid Flexor Tenosynovitis | PreOp ☐ | PostOp ☐ |
| 813.41 | Distal Radius Fracture-Extra articular | PreOp ☑ | PostOp ☑ |
| 813.42 | Distal Radius Fracture-Intra articular | PreOp ☐ | PostOp ☐ |
| 727.89 | Infection- Tendon Bursae/Sheaths | PreOp ☐ | PostOp ☑ |
| 215.2 | Mass in carpal canal- Benign | PreOp ☐ | PostOp ☐ |
| 955.1 | Direct Median Nerve Injury | PreOp ☐ | PostOp ☐ |
| | | PreOp ☐ | PostOp ☐ |

A confidential mEdisonOnline transaction for Doc M. Test, MD
contact by email https://www.medisononline.net/4DACTION/PickCPTMenu/Step1       11/19/2001

Fig. 15F

Enter Event Detail Part 1                                                                 Page 1 of 2 mEdisonOnline

Enter Event Detail

| Physician | Doc M. Test, MD | | Patient | BARBARA B SMITH |
|---|---|---|---|---|
| Hospital | Fairview-University Medical Center | | Date | 11/19/2001 |
| Incision Start | 00:00 | | Incision Close | 00:00 |
| Side | Right | | Assisting | None |
| CPT | 64721 Neuroplasty and/or transposition: wrist median nerve at carpal tunnel | | | |

Anesthesia | GA Mask |

Anesthesia Class

| ⦿ | ○ | ○ | ○ | ○ |
|---|---|---|---|---|
| I | II | III | IV | V |

Unexpected Events | None |

Est Blood Loss

| ⦿ | ○ | ○ | ○ |
|---|---|---|---|
| 0-30 | 11-50 | 50-200 | |

Preparation | Duraprep |   Latex Free Environment ☐

Drape | Arm Board |

Tournequet | Forearm |   Tournequet Time | |

Equipment | Scalpel Blade |

Other Equipment: | |

<u>Technique:</u>

Incision
| One: open method, across wrist crease |

<u>Pathology:</u>

Findings
| Normal appearance |

In op testing
| Normal Geyser test |

Nerve
| No adhesions |

Pathology Comments:

https://www.medisononline.net/4DACTION/LoopPost/                             11/19/2001

Fig.15G

Enter Event Detail Part 1            Page 2 of 2

Discharge Data Sent to Recovery, Dressing complete, DC to home

Follow up in days:

Abilities Data Sling, No Use

Notes:

A confidential mEdisonOnline transaction for Doc M. Test, MD
contact by email https://www.medisononline.net/4DACTION/LoopPost/      11/19/2001

Fig.15H

Operative Note                                                          Page 1 of 2

OPERATIVE REPORT
HOSPITAL: Fairview-University Medical Center

|  |  |
|---|---|
| Patient Name: | BARBARA B SMITH |
| MR#: | |
| DOB: | 03/12/1945 |
| Procedure Date: | 11/19/2001 |

PROCEDURE: 64721 Neuroplasty and/or transposition: wrist median nerve at carpal tunnel
Side: Right Diagnosis:
PREOPERATIVE
714 Rheumatoid Flexor Tenosynovitis
POSTOPERATIVE
714 Rheumatoid Flexor Tenosynovitis
727.89 Infection- Tendon Bursae/Sheaths Incision Start: 00:00   Incision Close: 00:00
Anesthesia: GA Mask   Anesthesia class: I
Complications: None
Estimated Blood Loss: 0-30
Preparation: Duraprep   Drape: Arm Board
Equipment: Scalpel Blade
Tourniquet: Forearm   Tourniquet Time:

OPERATIVE PATHOLOGY:
Findings: Normal appearance
In op testing: Normal Geyser test
Nerve: No adhesions TECHNIQUE:
Closure:
Incision: One: open method, across wrist crease
Incision Irrigation:
Ligament Management:
Protective Measures:
Sub-cutaneous closure:

STAFF PHYSICIAN: Doc M. Test, MD
ASSISTING PHYSICIAN(s): None

REFERRING PHYSICIAN(s): None

Event Key:00000HH

Created using mEdisonOnline
Confidential document. This may be printed by owner or licensee only.

https://www.medisononline.net/4DACTION/LoopPost/                        11/19/2001

Fig.15I-1

Operative Note                                                              Page 2 of 2 https://www.medisononline.net/4DACTION/LoopPost/                    11/19/2001

Discharge Orders                                                                 Page 1 of 1

Discharge Order
HOSPITAL: Fairview-University Medical Center

| | |
|---|---|
| Patient Name: | BARBARA B SMITH |
| MR#: | |
| DOB: | 03/12/1945 |
| Procedure Date: | 11/19/2001 |

PROCEDURE: 64721 Neuroplasty and/or transposition: wrist median nerve at carpal tunnel
Side: Right

DISCHARGE DATA:
Sent to Recovery, Dressing complete, DC to home

ABILITIES:
Sling, No Use

STAFF PHYSICIAN: Doc M. Test, MD
ASSISTING PHYSICIAN(s): None

REFERRING PHYSICIAN(s): None

Event Key:00000HH

Created using mEdisonOnline
Confidential document. This may be printed by owner or licensee only.

https://www.medisononline.net/4DACTION/LoopPost/                              11/19/2001

Fig. 15J mEdisonOnline Confidential                                    10/14/01

Neuroplasty:median nerve at carpal tunnel(2)
Abbrv.- Carpal Tunnel Release

Last Updated 05/25/2001

Linked/likely ICD-9's

| CPT | ICD-9 | Description |
|---|---|---|
| 64721 | 354 | Median neuropathy at Carpal Tunnel |
| 64721 | 714 | Rheumatoid Flexor Tenosynovitis |
| 64721 | 813.41 | Distal Radius Fracture-Extra articular |
| 64721 | 813.42 | Distal Radius Fracture-Intra articular |
| 64721 | 727.89 | Infection- Tendon Bursae/Sheaths |
| 64721 | 215.2 | Mass in carpal canal- Benign |
| 64721 | 955.1 | Direct Median Nerve injury |

Tournequet

| CPT | Group | Description |
|---|---|---|
| 64721 | T | Upper arm |
| 64721 | T | Forearm |
| 64721 | T | Bier Block |
| 64721 | T | None |

Drape Method

| CPT | Group | Description |
|---|---|---|
| 64721 | D | Arm Board |
| 64721 | D | Hand Table |
| 64721 | D | Cloth: Arm Only |
| 64721 | D | Paper: Arm Only |
| 64721 | D | Cloth: Whole Body |
| 64721 | D | Paper: Whole Body |

Equipment

| CPT | Group | Description |
|---|---|---|
| 64721 | Device | Scalpel Blade |

Page 1 of 3

Fig.16A mEdisonOnline Confidential                                    10/14/01

| CPT | Group | Description |
|---|---|---|
| 64721 | Device | Agee system |
| 64721 | Device | ECTRA system |
| 64721 | Device | IndianaTome |
| 64721 | Device | GRS:Guided Release System |

PATHOLOGY

| CPT | Group | Description |
|---|---|---|
| 64721 | Findings | Normal appearance |
| 64721 | Findings | Ganglion |
| 64721 | Findings | Flexor Synovitis |
| 64721 | Findings | Comments |
| 64721 | Findings | Lipoma |
| 64721 | Nerve | No adhesions |
| 64721 | Nerve | adhesed to surrounding tissue |
| 64721 | Nerve | Bifid |
| 64721 | Nerve | TransLigamentous Rec. motor branch |
| 64721 | Nerve | Neuroma in-continuity |
| 64721 | Nerve | Neuroma discontinuous |
| 64721 | In op testing | Normal Geyser test |
| 64721 | In op testing | Nerve Stimulator- motor response |
| 64721 | In op testing | Nerve Stimulator- no response |

TECHNIQUE

| CPT | Group | Description |
|---|---|---|
| 67421 | Incision | One: open method, across wrist crease |
| 67421 | Incision | One: open method, hand only |
| 67421 | Incision | One: Endo, distal portal |
| 67421 | Incision | One: Endo, proximal portal |
| 67421 | Incision | Two: Endo or Guide, Bi-portal |
| 67421 | Protective Measures | None |
| 67421 | Protective Measures | Blunt Disection |
| 67421 | Protective Measures | Superficial Palmar Arch Seen |
| 67421 | Protective Measures | Nerve Traced below thru carpal tunnel |
| 67421 | Ligament Management | ligament released by open visualization |

Page 2 of 3

16B mEdisonOnline Confidential                                          10/14/01

| | | |
|---|---|---|
| 67421 | Ligament Management | ligament released after endoscopic visualization |
| 67421 | Ligament Management | ligament released after guide placement |
| 64721 | Incision Irrigation | None |
| 67421 | Incision Irrigation | Incision(s) irrigated using physiologic solution (with antibiotics) |
| 67421 | Incision Irrigation | Incision(s) irrigated using physiologic solution (no antibiotics) |
| 64721 | Sub-cutaneous closure | None |
| 64721 | Sub-cutaneous closure | Interrupted sub-cutaneous closure |
| 67421 | Closure | Incision packed open |
| 67421 | Closure | Incision(s) closed, interupted "nylon" sutures |
| 67421 | Closure | Incision(s) closed, interupted absorbing sutures |
| 67421 | Closure | Incision(s) closed, sub-cuticular "nylon" sutures |
| 67421 | Closure | Incision(s) closed, sub-cuticular absorbing sutures |

DISCHARGE DATA

| CPT | Group | Description |
|---|---|---|
| 64721 | Recovery Room | Sent to Recovery, Dressing complete, DC to home |
| 64721 | Recovery Room | Sent to Recovery, Dressing and Temporary drain, DC to home |
| 64721 | Recovery Room | Sent to Recovery, admit to floor |
| 64721 | Out-patient Nurse Station | DC, FU in ____days, MD contact instructions, Anti-Pain Medicine prescription |
| 64721 | Admit to floor | Observe Hospital Order sheet |

Unexpected Events

| CPT | Group | Description |
|---|---|---|
| 64720 | Event | None |
| 64721 | Event | Operative Nerve Injury |
| 64721 | Event | Operative Tendon Injury |

Abilties Data (Work Compensation only)

| CPT | Group | Description |
|---|---|---|
| 64721 | Activity | Sling, No Use |
| 64721 | Activity | Use for ADL's only |
| 64721 | Activity | Light use for work assist OK: no grip, torque, reptition |

Page 3 of 3

16C

METHOD AND APPARATUS FOR OPERATIVE EVENT DOCUMENTATION AND RELATED DATA MANAGEMENT

RELATED APPLICATION

This application claims the benefit of priority to U.S. Provisional Patent Application Ser. No. 60/334,194, filed Nov. 29, 2001, of which is herein incorporated by reference in its entirety.

TECHNICAL FIELD OF THE INVENTION

This invention pertains generally to the field of medical documentation, and more particularly to method and apparatus for operative event documentation, storage and access.

BACKGROUND OF THE INVENTION

As many as 72 million surgical procedures are performed in the United States each year. For every one of these procedures, information about the diagnoses, treatment and relevant procedure documentation must be captured. A major problem in this information capture is that different entities need the same data but they capture the data in different ways and at different times due to a disjointed health care information structure with no one master.

Before a physician performs surgery in a hospital or outpatient clinic, basic information about the procedure is captured first for the hospitals (or clinics) operating room/suite system. This is usually done in an analog manner via telephone. This data, collected by the MD's office, is needed for the hospital to plan the procedure, but it is not generated in a consistent, standard, or legible fashion. Once an Operative Event has been completed the physician or her/his assistant completes dictation into a tape bank that will later be transcribed into an operative note. To be maximally useful, these notes should be transcribed and added to the patients' record immediately. However, it is common for the "draft" note to be outstanding for five or more days. Thus, it is uncommon for a hospitalized patient to have a real and/or complete Operative (event) Note in their chart during the hospital stay. Accordingly, the JCAHO (Joint Commission for Accreditation of Healthcare Organizations) requires that some minimal information be "Hand Written" in to the hospital chart. Once the note is transcribed, it is added to the patients' record, but it is not "official" until the physician who performed the operation reads the operative note and corrects any errors. About 20-40% of these initial operative notes need changes. Once the operative note is corrected and signed by the physician, the "draft" note is removed from the patients' medical record and replaced with the signed operative note. Separately, getting the notes to and from the physician is a significant problem for hospital medical records departments and for the physicians/physician offices. Not surprisingly, a percentage of operative notes go missing-in-action. These MIA notes are a large portion of the hospital's focus when it is required to complete an audit of its system by the JCAHO every three years. Most importantly, the lack of timely availability of an accurate operative note for the use of involved parties, leads to billing delays and errors causing payment delays, denials, and reductions to all interested parties.

It is a universal requirement that a record of surgery be created. This record is created for three purposes:
1. To comply with facility/governmental requirements;
2. To provide documentation of procedure completion for insurers; and
3. To facilitate future or current disease/procedure specific research.

Physicians using current analog/dictation methods do not routinely consult the coding texts which their office-clinic and the hospitals billing department use to numerically describe to the insurers the procedures and diagnosis for a given patient. Consequently, operative/procedure notes do not always match the codes that should be used to describe a specific event. Additionally, current dictation methods do not assist a single and certainly not a group of physicians to describe a procedure(s) in a consistent/reproducible fashion. Of additional importance, more than one group (Hospital, Proceduralist, Anesthesiologist, Pathologist, Radiologist) is often coding the same event independently. This creates more than a little confusion for the insurer looking at a bill for a particular patient who received treatment from three or more distinct entities, for example the 1) hospital, 2) anesthesiologist, 3) pathologist, and 4) surgeon, all on the same day which by report is for varying diagnosis with varying treatments. Variations in dictation combined with coding variations can also result in wide variations in how the physician is paid by insurance companies. Finally, because the current data is inconsistent, not a database, and not readily available to the physicians, it cannot be used by the physician to improve care, facilitate marketing, or enhance re-licensing usage without separate time consuming data entry.

There are a number of systems in the marketplace that allow for the entry of procedure information. These systems range from low cost Palm Pilot based systems to online billing systems. These systems have several major flaws. The Palm based systems are expecting the physician to significantly change their behavior in order utilize their software. They are complex and cumbersome to use and provide little value to the physician, other than a portable subset of the patients' record. These systems do not integrate into existing systems and other than early adopter "geek doctors", have not succeeded in the market. The existing billing systems are designed as accounting first and an easy way to input procedure information last or not at all. Billing systems are also different between the hospital and the doctors' offices, thus information is consistent only by random luck.

Accordingly, there is considerable room for improvement in the area of operative event documentation and the storage and use of the associated data.

SUMMARY OF THE INVENTION

According to one aspect of the invention, there is provided a method and apparatus for operative event documentation wherein the documentation procedure is simplified and streamlined.

According to another aspect of the invention, there is provided method and apparatus for managing operative event documentation data, including the ownership, control and use of that data.

BRIEF DESCRIPTION OF THE DRAWINGS

FIGS. 15A-J illustrate a user interface (UI) according to one example embodiment of the invention, wherein FIGS. 15G and H illustrate a further event documentation input screen, and wherein FIGS. 15I-1, I-2 and J illustrate example embodiments of operative discharge reports.

FIGS. 16A-C illustrate an example embodiment of the invention in which a cross reference table shows the cross referencing of CPT codes to ICD9 codes and other documentation.

DETAILED DESCRIPTION OF THE INVENTION

In the following detailed description of the embodiments, reference is made to the accompanying drawings which form a part hereof, and in which is shown by way of illustration specific embodiments in which the invention may be practiced. It is to be understood that other embodiments may be utilized and structural changes may be made without departing from the scope of the present invention.

Methods of the Invention

Figure 1:
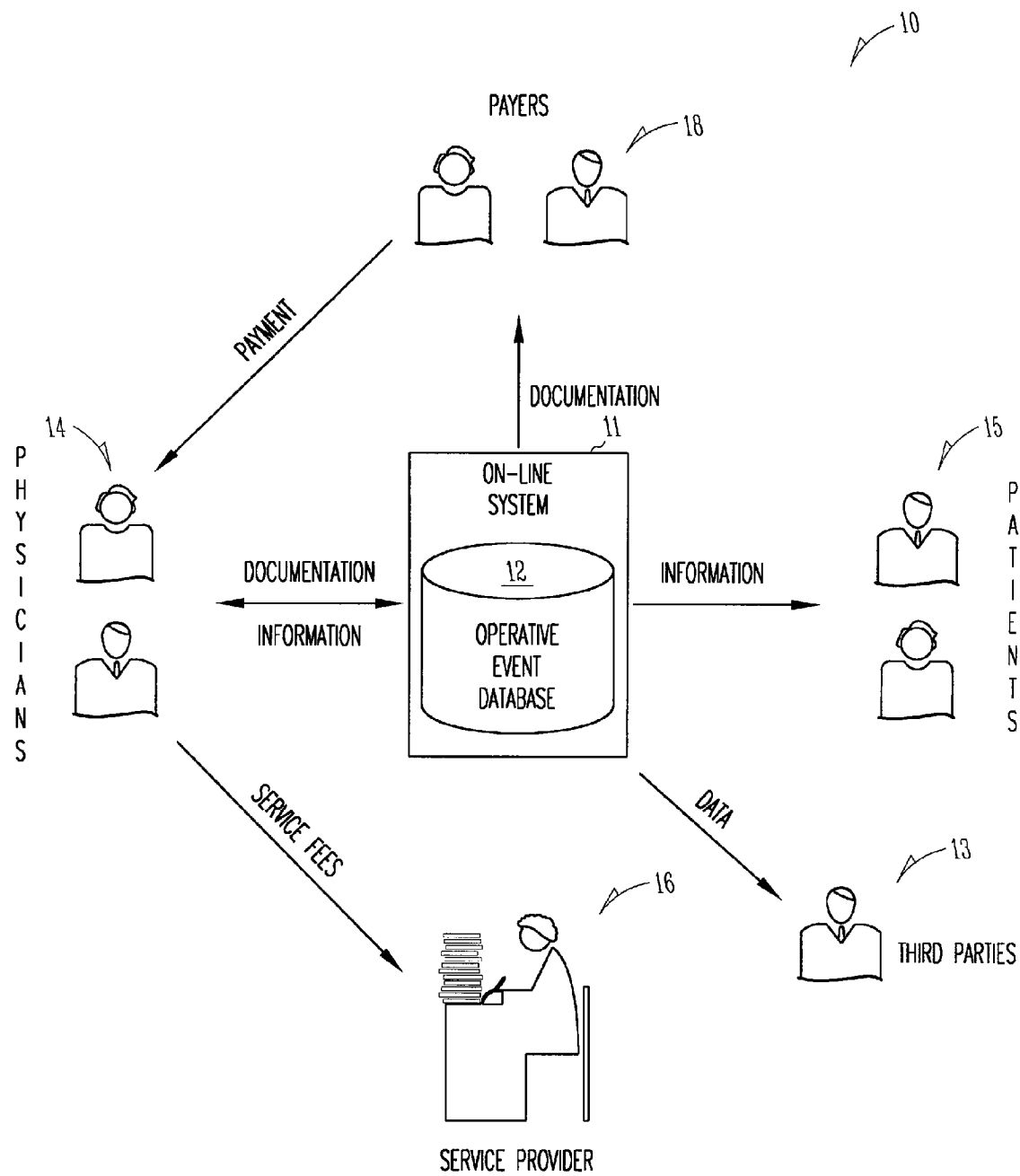
FIG. 1 illustrates a first embodiment of the method of the invention, wherein the method provides that a plurality of physicians enter operative event data into an operative event database and the operative event data documents planned or completed operative events.

Referring now to FIG. 1, there is illustrated a first embodiment 10 of the method of the invention. According to this embodiment, the method provides that a plurality of physicians 14 enter operative event data into an operative event database 12, wherein the operative event data documents planned or completed operative events. Physicians entering the operative event data use a wide area network, such as the Internet, through a user interface, for example web-enabled, assisting the physicians in coding operative events in a consistent manner. Physicians access the operative event database to obtain information concerning upcoming or previously performed operative events. A service provider 16 maintains an on-line system 11 including one or more servers to support the entering of operative event data into the database through the Internet and the user interface. Further, physicians subscribe to the on-line system wherein the physicians such that the subscribing physicians are allowed access and use the on-line system. In addition, the physicians retain control over the use and disposition of the operative event data entered by the physician. According to this embodiment, the operative event data is entered either by the physician or by an assistant for the physician.

According to another example embodiment, the operative event data is used to obtain payment from a payer 18 for medical services rendered. In another embodiment, more than one physician uses the system to enter coding for different medical services rendered in connection with the same operative event, and the system assists in conforming one of the codings for an operative event to another coding for the same operative event.

According to still another example embodiment of the method of the invention, at least some of the operative event data is made available to third parties 13 such as hospitals or research operations, and additionally the operative event data is made available so that any patient identifying information is omitted.

According to yet still another example embodiment, the operative event data is made available in summary form, or according to geographical areas.

In yet another embodiment, the operative event data for a subscriber physician is made available to actual or potential patients 15.

In yet still another embodiment of the methods of the invention, patient outcome data is entered into the system and the outcome data is correlated with coded operative events. Further, in yet another embodiment, a summary of operative event data and associated outcomes for a subscriber physician is made available to potential patients 15. In another embodiment, coded operative events are reported by frequency of diagnosis, procedure, age distribution, and satisfaction index. Further, such reports are, in one embodiment, provided to a physician office, hospital or designated copy sites for use or distribution.

According to still another embodiment, coded operative events for a plurality of physicians are combined to form a group report. In one such example, an individual physician's coded operative events are summarized and compared with a group summary.

According to another example embodiment, similar coded operative events for different patients and associated outcomes are collected as part of a study and the collected data reported to allow tracking of a study.

According to yet another example embodiment, patient satisfaction data are input into the system wherein the patient satisfaction data corresponds to operative events. According to such an embodiment, patient satisfaction data is reported and the reporting is obtained on-line by a prospective patient.

According to yet still another example embodiment, the physician electronically signs the operative note.

In still another example embodiment or the methods of the invention, physicians pay a fee to the service provider based on the entry of an operative note into the system or other criteria. In yet still another embodiment, the system downloads an operative note to a hospital and the hospital pays a fee to the service provider for downloading an operative note.

According to yet another example embodiment, the system generates discharge reports from the system in response at least in part to the operative event data entered by physicians, and such reports are used by a hospital or clinic treating a discharged patient paying the service provider a fee for each discharge report. In yet another embodiment, a physician or other non-physician entity pays the service provider an annual charge for access to the system.

Figure 2:
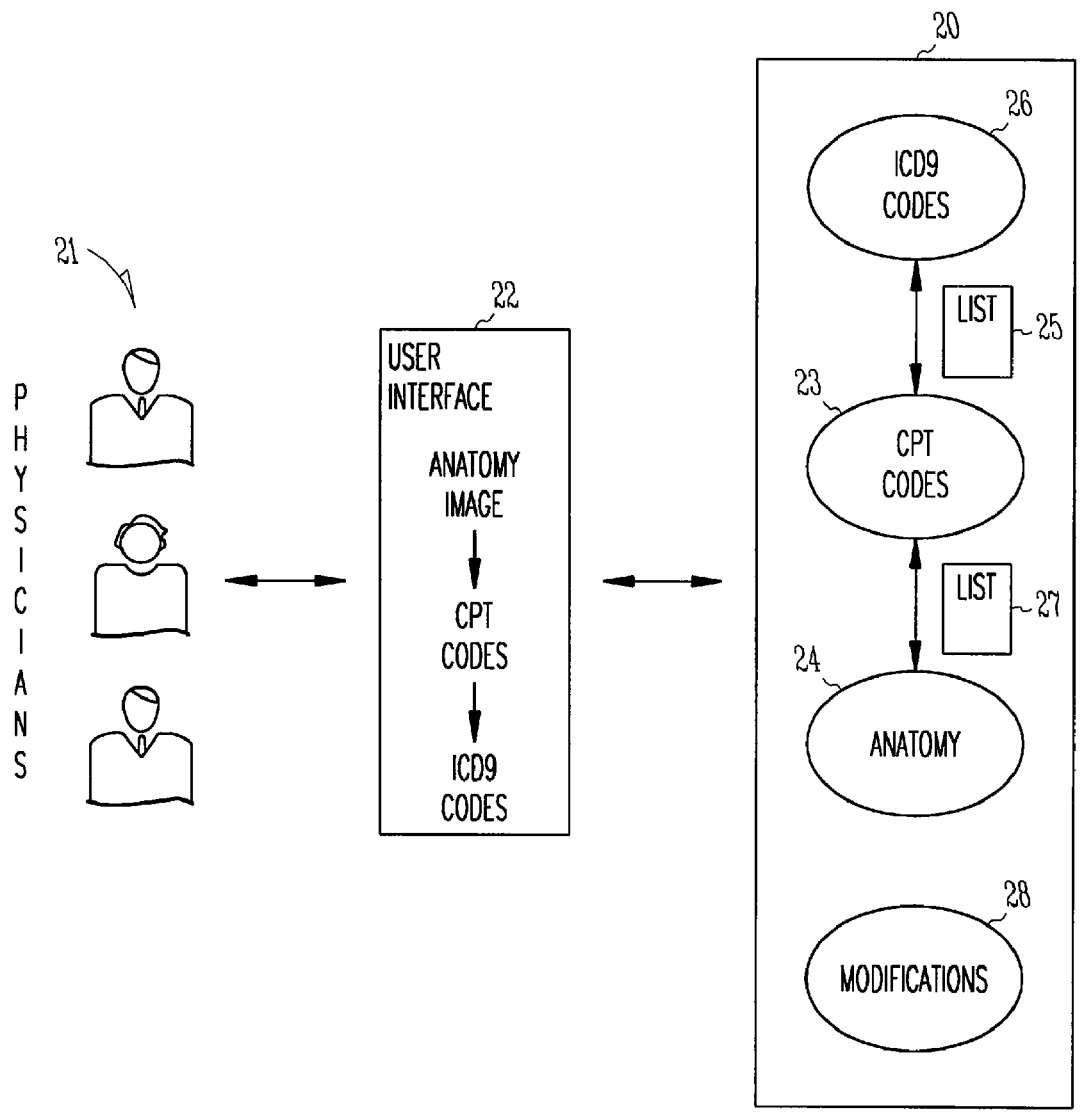
FIG. 2 illustrates an embodiment of a method of the invention that provides for a plurality of physicians each entering operative event data into an operative event database system, wherein the operative event data documents planned or completed operative events.

According to still another example embodiment illustrated in FIG. 2, a method of the invention provides for a plurality of physicians 21 each entering operative event data into an operative event database system 20, wherein the operative event data documents planned or completed operative events. The physicians enter the operative event data using a wide area network through a user interface 22 assisting the physicians in coding operative events in a consistent manner. The operative event database system 20 includes a library of CPT codes 23 cross-referenced to a region of an anatomy 24. A physician uses the user interface to select a region of the anatomy from an image of the anatomy displayed to the physician. A list 25 of CPT codes are displayed to the physician such that is substantially comprised of CPT codes cross-referenced to the selected region. The physician picks at least one of the CPT codes from the list for the purpose of documenting an operative event. Further, an assistant may select the CPT code for the physician.

In still another example embodiment further including patient demographic data stored in the system for each patient for which a coded operative event has been entered in the system. ICD9 codes 26 are stored in the system wherein the ICD9 codes are cross-referenced to CPT codes. A list 27 of ICD9 codes are disclosed to a physician wherein the list of ICD9 codes comprises ICD9 codes cross-referenced to the CPT codes.

In yet still another embodiment, a physician first selects a CPT code, which in turn is cross-referenced to one or more ICD9 codes that are displayed to the user for selection, so that an operative event is documented with CPT and ICD9 codes. The system requests further event detail information from the physician based on the CPT and ICD9 codes selected by the physician to document the event, wherein the requested information changes at least in some cases based on the selected CPT and ICD9 codes.

According to yet another example embodiment, detail information is entered, wherein the event detail is selected from the group of: anesthesia and preparation information, technique, pathology, in-patient discharge information, outpatient discharge information, and worker's compensation/abilities information.

In yet another exemplary embodiment, a physician can modify the list of CPT or ICD9 codes to create a set of modification data 28 that are displayed such that the codes are customized to a particular physician's practice.

In yet another example embodiment, printed reports, electronic reports or electronic downloads of operative event data from the system are reported. According to this example embodiment, the code entering physician views and accesses his or her data only.

In yet still another example embodiment of the invention, users search for CPT or ICD9 codes using a few front end letters and see choices appear in a menu.

Figure 3:
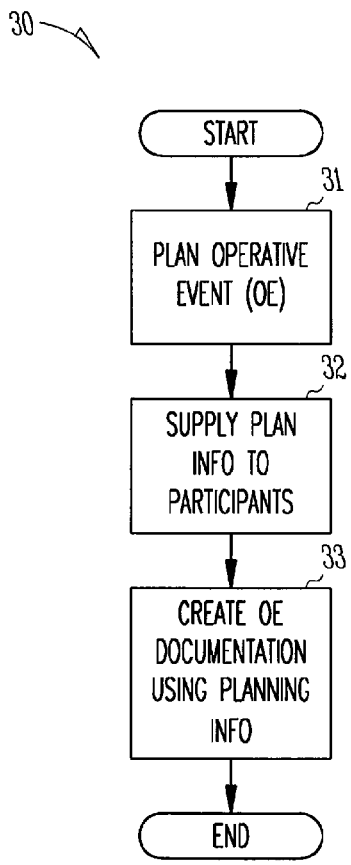
FIG. 3 illustrates operative events that are first planned in the system the actual operative event.

According to still another example embodiment 30 shown in FIG. 3, operative events are first planned 31 in the system, information is then suppied to participants 32, and then the plan is used at least in part to create the documentation 33 of the actual operative event. Thus, in one example embodiment, when the surgery is planned, equipment lists, diagnosis, and baseline data are chosen and the information is supplied to the participants in actual surgical event. Accordingly, the planned operative event information is accessed from the on-line system by personnel such as the planning physician and the planning information is used to prepare the operating facility for the operation and carry out the invention. Further, the operative event documentation from the event itself are used by further personnel for example to reimburse the medical personnel or facility, or to follow the outcome of a patient for study purposes or for worker's compensation purposes or others.

Figure 4:
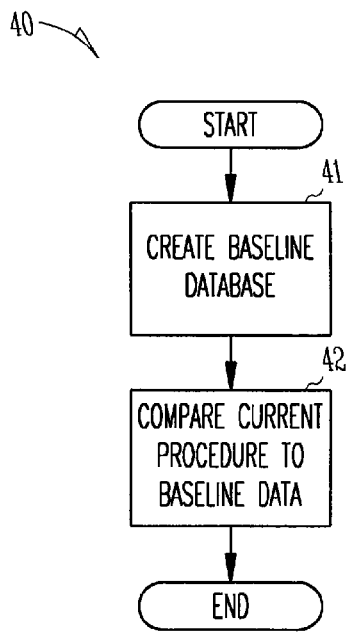
FIG. 4 illustrates an embodiment of the invention in which there is created and maintained a baseline database of operative event and post operative data which can be compared to operative and post operative data from ongoing surgical events.

According to still another embodiment 40 of the invention illustrated in FIG. 4, there is created and maintained a baseline database 41 of operative event and post operative data which can be compared to operative and post operative data from ongoing surgical events 42. The data can be compared against issues such as worker's compensation.

Figure 5:
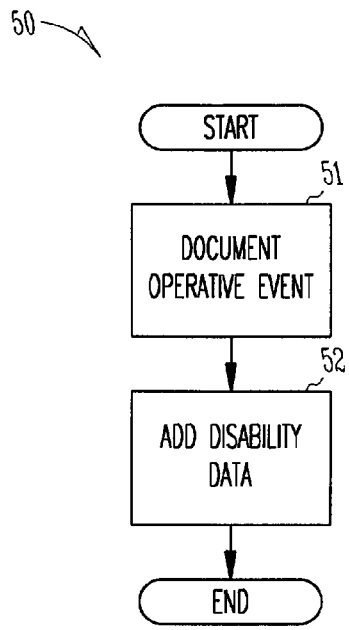
FIG. 5 illustrates an embodiment of the invention wherein a system provides connectedness of operative procedures for workers to ultimate disability ratings.

According to still another embodiment 50 of the method of the invention illustrated in FIG. 5, the system provided connectedness of operative procedures for workers to ultimate disability ratings. Using the online operative data 51, this disabilities tracker allows physicians to achieve timely closure of work cases and easy tracking of workers abilities and final outcomes 52 (these are two different things as a worker can have lost function and received a settlement yet returned to original work duty without restriction).

According to another embodiment of the method of the invention, there is provided a record of relatedness of procedure to operative consent, surgical planning per hospital, discharge planning per hospital, and patient's language. To the degree possible, the patient is presented materials in their first language using language specific templates.

Figure 6:
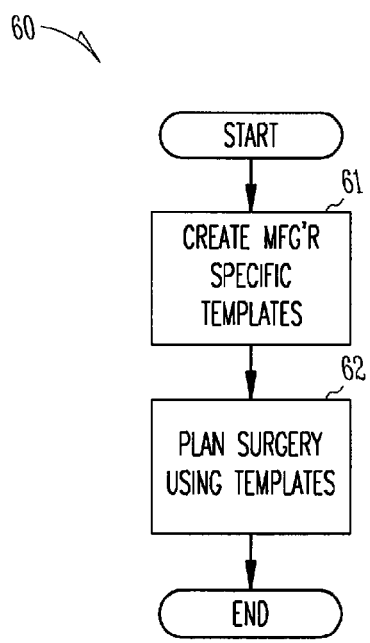
FIG. 6 illustrates an embodiment of the invention in which surgery is planned from manufacturer-specific templates for implant procedures.

According to yet another example embodiment 60 illustrated in FIG. 6, surgery is planned from manufacturer-specific templates for implant procedures. For example, each manufacturer of an implant device may have associated with it one or more predefined templates 61 stored in the system database that a health care professional can use to create a surgical plan. Thus, implant specific plans can be readily prepared 62 using the templates. In one embodiment, "sized" x-rays are imported into system pre planning modules, and compared to a selected template and then sent to the and/or manufacturer/operating room equipment storage location.

According to yet another example embodiment, alert functions track pending pathology for specimen cases and "tack" result to operative results for "final" approval or action.

According to still another embodiment, alert functions for a physician or other health care provider let a radiologist know if the operative findings did not correlate with a radiological diagnosis.

According to still another example embodiment of the invention, the documenting physician enters a "grade" for a resident's technical skill or the skills of any other assisting personnel. Such grades or rankings are preferably kept in the operative event database such that the grades or rankings are viewable only selectively by the entering physician and any one else he or she authorizes to see the grades or rankings, and are otherwise not available to other parties accessing the system.

Thus, as described above, the embodiments of the present invention provide for:

1) A CPT code "shopping cart";
2) An operative summary method;
3) An ability to link CPT's and ICD's;
4) An ability to "learn" the physicians method;
5) An ability for individual user personnel to locally modify parts of event/operative technique;
6) An ability to generate summary reports easily;
7) An ability to add therapy and discharge prescription orders to the discharge summary; and
8) An ability to import data to billing and EMR software packages.

Figure 7:
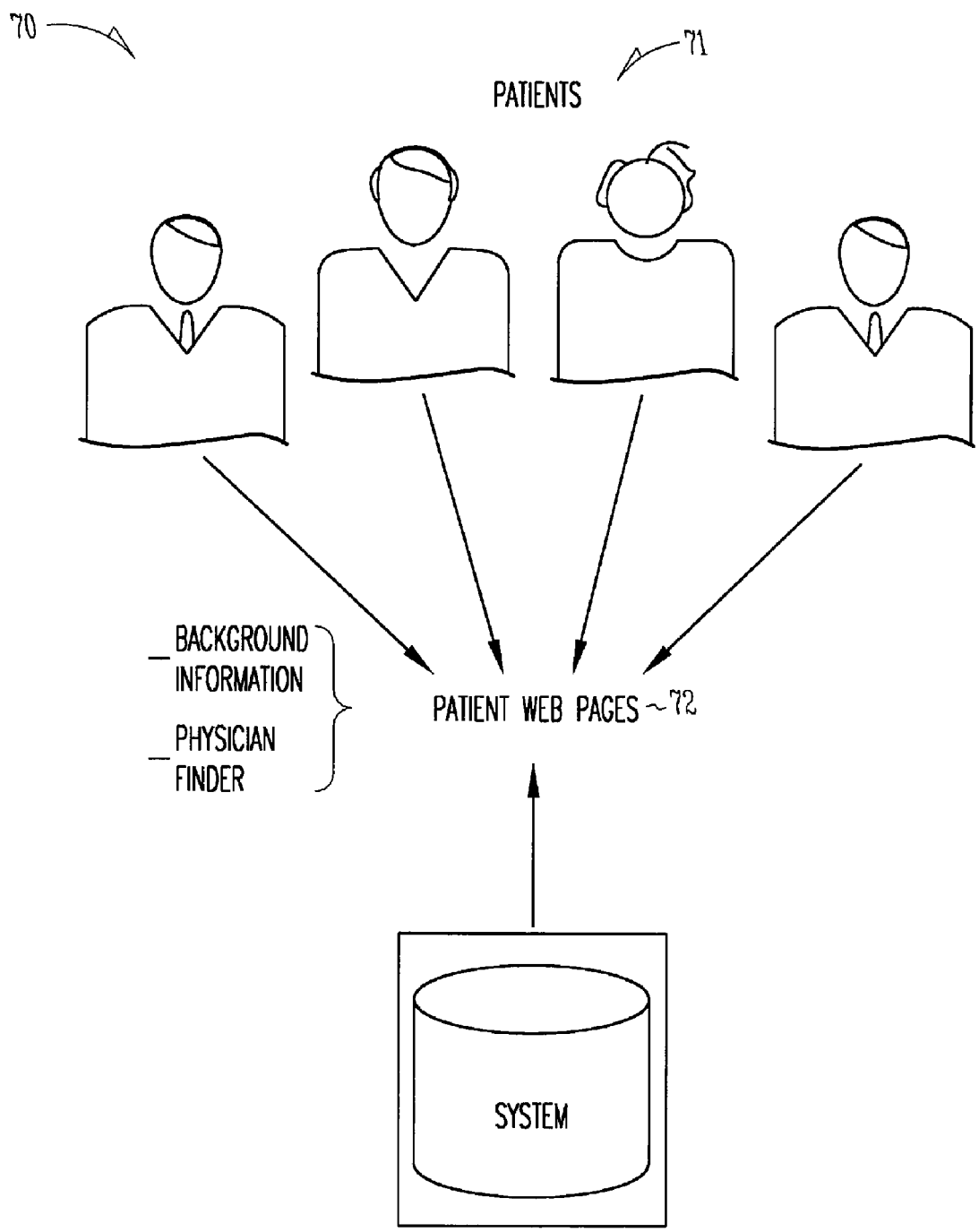
FIG. 7 illustrates an embodiment of the invention which includes a patient web pages area of a web site that is a tool for patients to use.

According to still another embodiment 70 illustrated in FIG. 7, the system of the present invention includes a patient web pages area 72 of a web site that is a tool for patients 71 to use to understanding the frequency of diagnosis and any proposed procedure. In this embodiment some background information is available regards possible procedures. Specific emphasis is placed on procedural indications, contra-indications, goals, and common outcomes. One feature of this portion of the site is the physician finder. According to one example embodiment, participation in the physician finder is voluntary. Physicians who choose to participate must agree with the system provider to display their satisfaction data in one of two forms (as part of the regional aggregate or as part of the aggregate and individually). The site allows physicians who choose to participate in the satisfaction data, to promote themselves with "real" data (case summaries, National Library of Medicine summaries, Board certification, State Licensure). Satisfaction/outcome data from patients may be obtained by telephone, mail or e-mail survey instruments. The system provider can assemble this data and maintain its integrity.

According to one example embodiment, using the subscription portion of the patient access web site, a patient could query the database regards who has done at least 100 X-procedures/year with a 85% satisfaction rate and practices within 150 miles. The answer to this question is currently unavailable. But the answer is desired by ALL PATIENTS and by the physicians capable of achieving the desired result.

Figure 8:
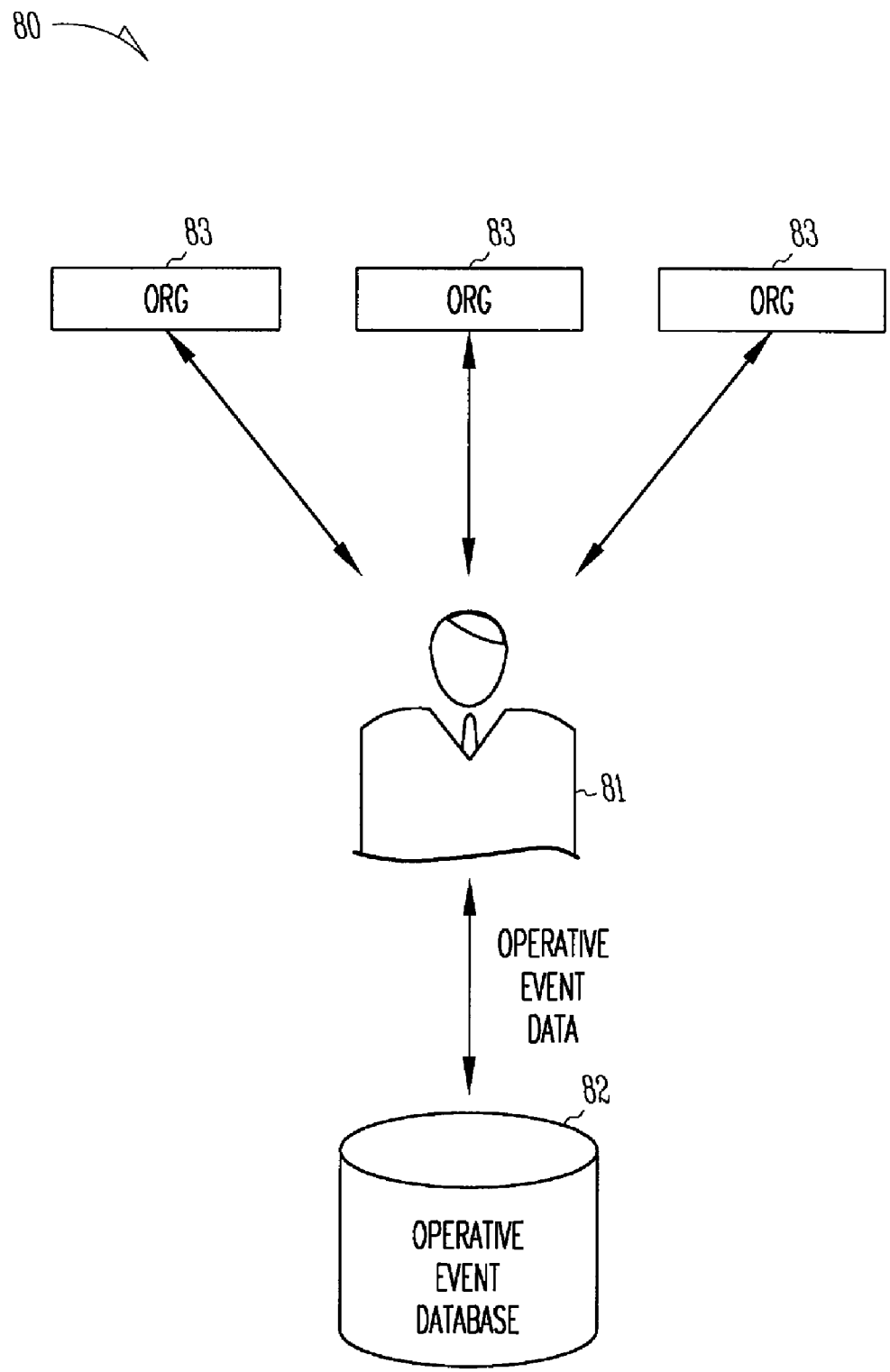
FIG. 8 illustrates an embodiment of the invention in which the system provides that a physician may enter operative event data for planning execution or follow up in a database for events that are associated with or are conducted at more than one clinic or hospital organization.

According to yet still another embodiment 80 illustrated in FIG. 8, the system of the present invention provides that a physician 81 may enter operative event data for planning execution or follow up in a central database 82 for events that are associated with or are conducted at more than one clinic or hospital organization 83. Thus, the physician/physician office documents, owns, distributes, and retrieves the critical components of an operative event, not the clinic or hospital at which the event is executed. The physician can later query her/his data from any web enabled device and design personal practice summaries, competitive practice summaries, and plan targeted practice growth. A physicians personal practice data is only specifically available to others to whom the physician allows access. This access can be time, region (hospital/practice), or site (anatomic) limited. This product contains x-links, specialized procedure picker, and specialized procedure templates, as described above.

Apparatus of the Invention

Figure 9:
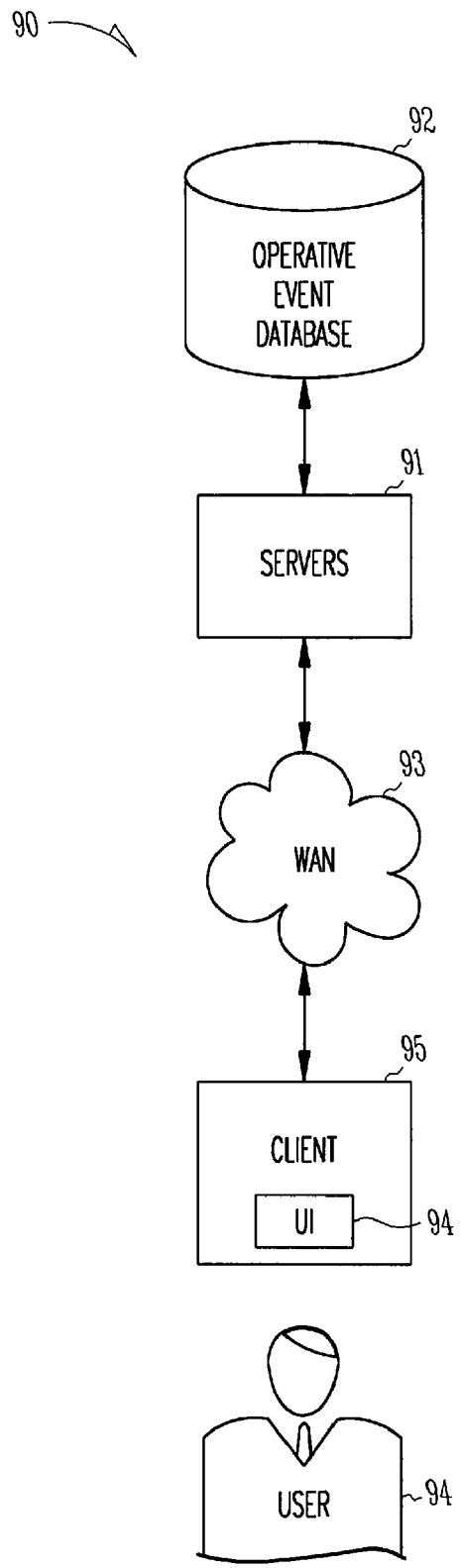
FIG. 9 illustrates an overview of an example embodiment according to the apparatus of the invention.
Figure 10:
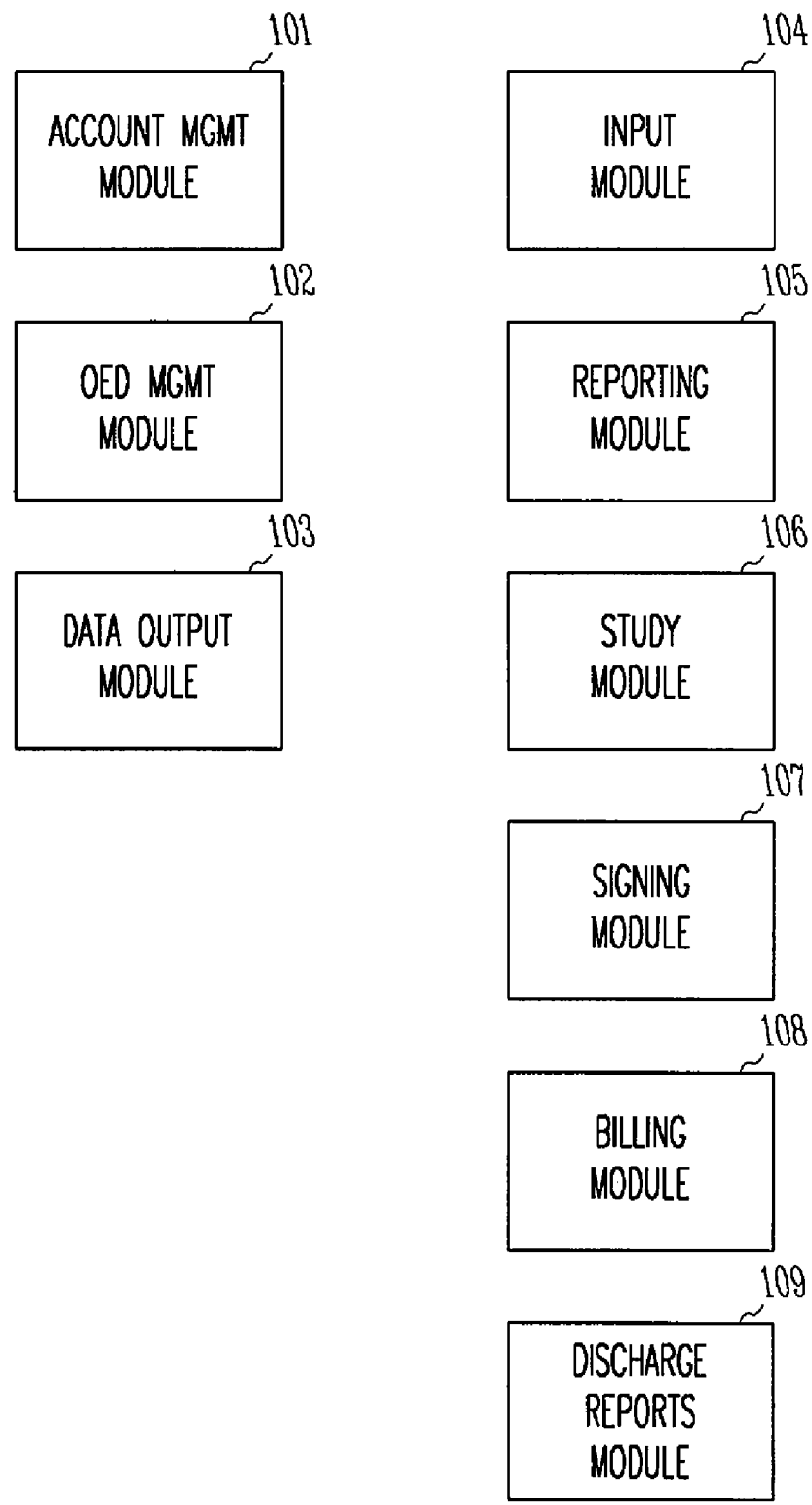
FIG. 10 illustrates an embodiment of an account management system which is operative on the one or more servers to maintain a list of subscribing physicians authorized to use the on-line system.

Referring now to FIG. 9, there is illustrated an overview of an example embodiment according to the apparatus of the invention. An on-line system 90 includes one or more servers to support the entering of operative event data into an operative event database 92 through a wide area network 93 and a user interface 94 presented on a client computer. The operative event database contains operative event data documenting planned or completed operative events performed by a plurality of physicians. A client computer 95 is connected to the one or more servers 91 through a wide area network. The interface is adapted to assist the physicians in coding operative events in a consistent manner. Referring to FIG. 10, an account management system 100 is operative on the one or more servers maintains a list of subscribing physicians authorized to use the on-line system. An operative event data management module 102 operative on the one or more servers allows authorized physicians to control the use and disposition of the operative event data entered by the physician in the on-line system. According to one example embodiment, an assistant enters operative event data for the physician.

According to yet another example embodiment, a system according to the apparatus of the invention further provides that the operative event data is used to obtain payment from a payer for medical services rendered.

In still yet another example embodiment of the invention, more than one physician to document different medical services rendered in connection with the same operative event enters the operative event data.

According to yet another example embodiment of the invention shown in FIG. 10, module 102 includes a data processing sub-module that assists in conforming one of the codings for an operative event to another coding for the same operative event. According to yet another example embodiment of the invention, a data output module outputs 103 at least some of the operative event data to third parties.

In yet another example embodiment of the invention, the operative event data is output without any patient identifying information, and the operative event data is output in summary form.

According to yet another example embodiment of the invention, the operative event data is output according to geographical areas. In yet another example embodiment of the invention, a prospective patient data output module makes operative event data for a subscriber physician available to potential patients.

In yet another example embodiment, there is provided an input and storage module 104 is provided for entering patient outcome data into the system and correlating the outcome data with coded operative events.

According to yet another example embodiment of the invention, a reporting module 105 makes at least a summary of operative event data and associated outcomes for a subscriber physician available to potential patients. Further, reporting module 105 reports operative events by frequency of diagnosis, procedure, age distribution, and satisfaction index. According to yet another example embodiment of the invention, reporting module 105 includes a sub-module for outputting coded operative event reports to a physician office, hospital or designated copy sites for use or distribution. According to yet another example embodiment of the invention, the reporting module 105 includes a sub-module for combining reporting coded operative events for a plurality of physicians to form a group report. In yet another example embodiment of the invention, the reporting module 105 includes a sub-module for comparing an individual physician's coded operative events summary with a group summary.

According to still yet another example embodiment of the invention, a study module 106 is provided for collecting similar coded operative events for different patients and associated outcomes as part of a study and reporting the collected data to allow tracking of a study.

In still another example embodiment of the invention, a input module 104 includes a satisfaction data input sub-module that receives patient satisfaction data into the system corresponding to operative events, and a satisfaction data output module is provided to output satisfaction data to interested parties.

According to yet another example embodiment of the invention, a signing module 107 enables a physician to electronically sign the operative note.

In yet still another example embodiment of the invention, a billing module 108 is provided for charging a physician a fee to the service provider based on the entry of an operative note into the system. The billing module includes a sub-module for charging a fee to a hospital for downloading an operative note.

In another example embodiment, a discharge-reporting module 109 generates discharge reports from the system in response at least in part to the operative event data entered by physicians.

According to yet another example embodiment of the invention, the billing module 108 includes a sub-module for billing a hospital or clinic treating a discharged patient a fee for each discharge report. In another embodiment, the billing module includes a sub-module for charging a physician or other entity an annual charge for access to the system.

Figure 11:
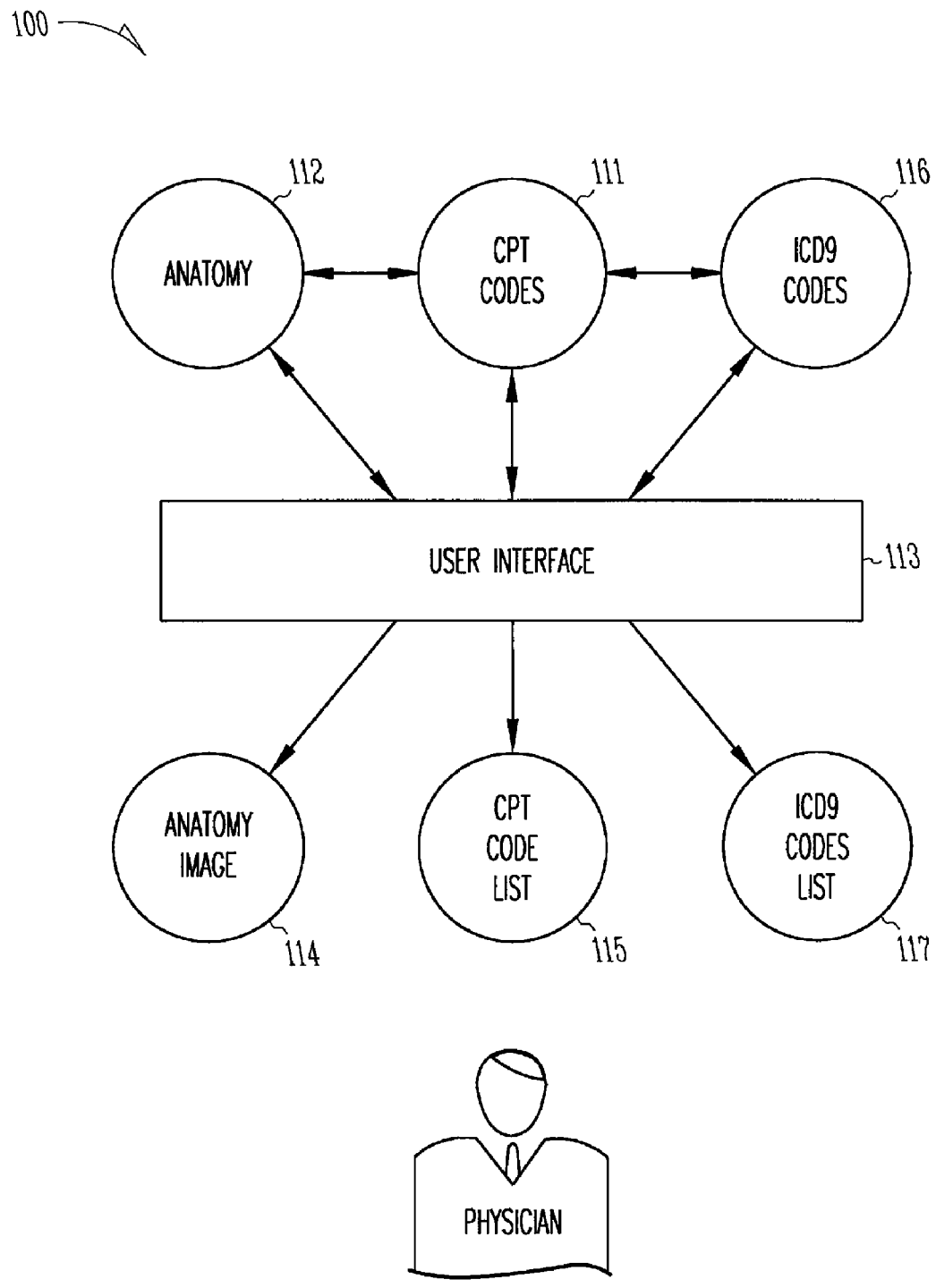
FIG. 11 illustrates an embodiment of the apparatus of the invention in which an operative event database system is provided, wherein the operative event data documents planned or completed operative events for a plurality of physicians.

In yet still another example embodiment 110 of the apparatus of the invention illustrated in FIG. 11, an operative event database system is provided, wherein the operative event data documents planned or completed operative events for a plurality of physicians. Further, the operative event database system including a library of CPT codes 111 cross-referenced to regions of an anatomy 112 and ICD9 codes 116, and a user interface 113 for the database system is adapted to permit a physician user to select a region of the anatomy from an image 114 of the anatomy displayed to the physician. The user interface 113 includes a sub-module for displaying to the physician a list 115 of CPT codes that is substantially comprised of CPT codes cross-referenced to the selected region. The user interface includes a sub-module adapted to allow a physician to pick at least one of the CPT codes from the list for the purpose of documenting an operative event.

According to yet another example embodiment of the invention, a sub-module is provided for storing patient demographic data in the system for each patient for whom a coded operative event has been entered in the system.

According to still yet another example embodiment of the invention, there is provided a sub-module for storing ICD9 codes 116 stored in the system wherein the ICD9 codes are cross-referenced to CPT codes 111. According to yet another example embodiment of the invention, a sub-module displays a list 117 of ICD9 codes to a physician wherein the list of ICD9 codes comprises ICD9 codes cross-referenced to the CPT codes. A sub-module allows the physician to select one or more ICD9 codes so that an operative event is documented with CPT and ICD9 codes.

According to yet another example embodiment of the a sub-module for requesting further event detail information from the physician based on the CPT and ICD9 codes selected by the physician to document the event, wherein the requested information changes at least in some cases based on the selected CPT and ICD9 codes.

Figure 12:
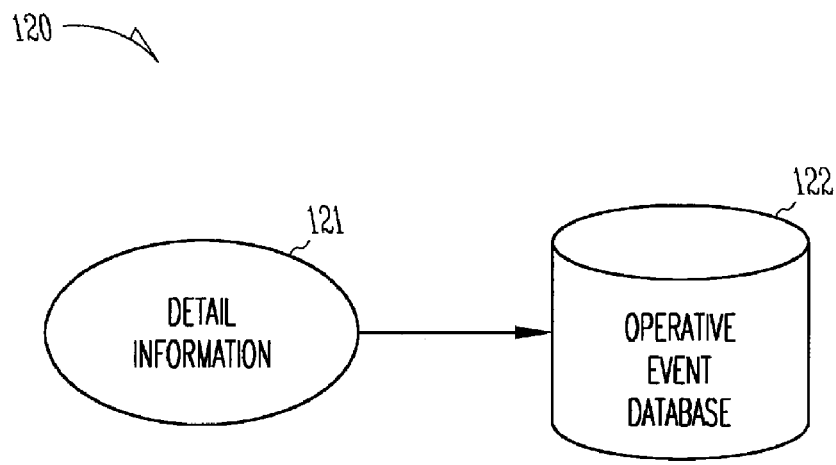
FIG. 12 illustrates an embodiment of the invention in which a sub-module for entering requested detail information is provided.

According to yet another example embodiment 120 of the invention illustrated in FIG. 12, there is provided a sub-module for entering requested detail information 121 and storing in operative event database 122. According to yet another example embodiment of the invention, the event detail is selected from the group of: anesthesia and preparation information, technique, pathology, in-patient discharge information, outpatient discharge information, and worker's compensation/abilities information.

Figure 13:
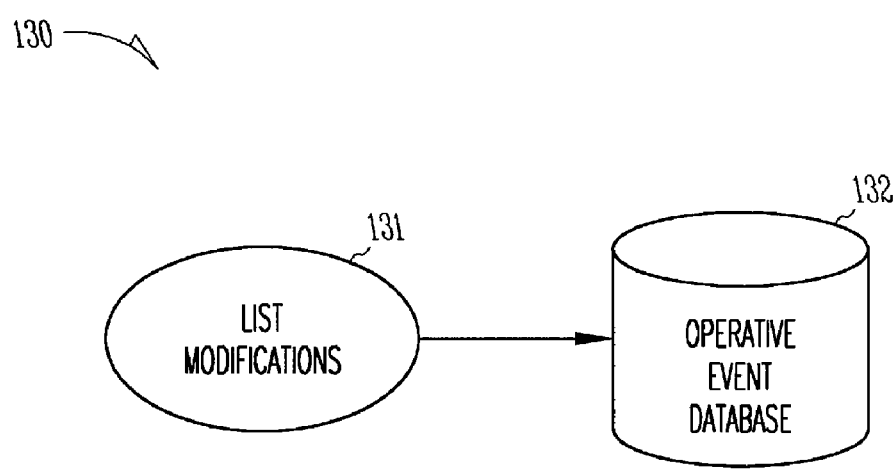
FIG. 13 illustrates an embodiment of the invention wherein a customization sub-module allows a physician or other user to modify the list of CPT or ICD9 codes are displayed such that the codes are customized to a particular physician's practice.

According to yet another example embodiment 130 of the invention shown in FIG. 13, a customization sub-module allowing a physician to modify 131 the list of CPT or ICD9 codes that are displayed such that the codes are customized 132 to a particular physician's practice.

In still yet another example embodiment of the invention, module 103 provides an output sub-module for outputting printed reports, electronic reports or electronic downloads of operative event data from the system.

According to yet another example embodiment of the invention, a sub-module is provided for allowing the code-entering physician to view and access his or her data only.

In yet still another example embodiment of the invention, a module 101 provides that users search for CPT or ICD codes using a few front end letters and see choices appear in a menu.

According to still another example embodiment, module 101 provides that operative events are first planned in the system, and then the plan is used at least in part to create the documentation of the actual operative event. Thus, when the surgery is planned, equipment lists, diagnosis, and baseline data is chosen which will flow to the actual surgical event. Accordingly, personnel such as the planning physician access the planned operative event information from the on-line system and the planning information is used to preparing the operating facility for the operation and carry out the invention. Further, the operative event documentation from the event itself are used by further personnel for example to reimburse the medical personnel or facility, or to follow the outcome of a patient for study purposes or for worker's compensation purposes or others.

According to still another aspect of the invention, module 101 provides for creating and maintaining a baseline database of operative event and postoperative data which can be compared to operative and postoperative data from ongoing surgical events. The data can be compared against issues such as worker's compensation According to still another aspect of the invention, module 101 provides that the system provides connectedness of operative procedures for workers to ultimate disability ratings. Using the operative data online, this disabilities tracker module allows physicians to achieve timely closure of work cases and easy tracking of workers abilities and final outcomes (these are two different things as a worker can have lost function and received a settlement yet returned to original work duty without restriction).

According to another embodiment of the apparatus of the invention, module 101 provides a record of relatedness of procedure to operative consent, surgical planning per hospital, and discharge planning per hospital, and patient's language. To the degree possible, the patient is presented materials in their first language using language specific templates.

According to yet another example embodiment of the apparatus, module 101 provides that surgery is planned from manufacturer-specific templates for implant procedures. For example, each manufacturer of an implant device may have associated with it one or more predefined templates stored in the system database that a health care professional can use to create a surgical plan. Thus, implant specific plans can be readily prepared. In one embodiment, "sized" x-rays are imported into system pre planning modules, and compared to a selected template and then sent to the and/or manufacturer/operating room storage location.

According to yet another example embodiment, alert functions module is provided and tracks pending pathology for specimen cases and "tack" result to operative results for "final" approval or action. According to still another embodiment, alert functions for a physician or other health care provider let a radiologist know if the operative findings did not correlate with a radiological diagnosis.

Thus, as described above, the various embodiments of the invention change the document creation method so that the creator/author retains primary control of the created data. Because the system is accessed online, the individual physicians account is available anywhere/anytime. Also, the present invention makes a "signed" created report available to all authorized parties immediately, regardless of location. Moreover, the cost to produce/access such a report is less than that which is currently incurred.

The long-term availability of physician data offers a value to individual physicians that are not currently available. The projected cost of offering this secure service makes the creation/maintenance of a similar database untenable for the average physician.

Additionally, the present invention can be used to facilitate procedure planning. That is, the physician can communicate to the operating room in advance the planned procedure and equipment requirements.

Finally, the present invention offers the individual physician an affordable means to collecting practice-wide satisfaction data, which can be displayed, competitively to the world.

According to some example embodiments, the method and apparatus of the invention provide an interactive web site, which is designed to take advantage of emerging technology and its widespread distribution. It can provide benefit to an individual practice or health system even before patients have gained routine access to the Internet. By way of some devices, the Internet site could interact with registered parties through wireless means even without a direct Internet connection. But, this wireless ability is just one method for accessing the Internet system. Using current jargon, the present invention is desirably implemented as an ASP (application service provider).

One advantage of the present invention is its ability to deliver and subsequently securely restore, a language/cultural specific visual interactive message, of a proven communications quality, to a worldwide audience simultaneously and individually, which saves the users money and time. This advantage over existing media is magnified by virtue of:
1. being individually customizable while at the same time up-dateable on a system-wide basis instantaneously,
2. being interactive with the patient, the caregivers, and potentially, third parties.
3. being "intelligent". This occurs in two ways: 1) the initial software product adapts itself to reflect the user's most common method of care delivery and 2) the user can "teach" the original database new data as long as it is entered following the established framework. This new data or method is unique to the individual who entered the new data. But because it is in specific fields it can still be compared to the whole experience.
4. This "intelligence" is able to instantaneously translate between a variety of languages. According to one example embodiment, the program may offer face-to-face language appropriate interaction.
5. Finally, the media can be customized to represent any health system directly. Thus, any provider or system can use the invention as their content provider for purposes of documenting surgical/operative care
6. The CPT Picker. This is analogous to a shopping cart. When a user MD/surgeon signs on to the on-line system, for example web site, of the invention, the physician is recognized as an orthopaedist, cardiac surgeon, or whatever, based on a profile for the physician maintained in the system. The screens seen from that point are type specific.

Thus, when the web page to pick CPT's is seen it makes sense based upon specialty and, unlike the CPT books, the spectrum of codes for a specific region are directly visible. Moreover, the codes are linked to correct ICD and RVU codes with care taken to cancel overlapping codes. This combined system places the most knowledgeable person at the front end of the description process regards "coding" the operative event. But, unlike some other methods, the method and apparatus of the present invention displays the critical data in user-friendly medical language while retaining back-office organization to assist in rapid preparation of code correct operative notes.
7. The shopping cart can handle a sufficient number of codes so that any patient event can be described.
8. The operative note engine of one example embodiment of the invention assembles the templates from data previously entered by MD experts and retained as part of continuously updated operative note content. These templates allow the MD to click/key/ and "speak"(assume voice recognition available) the notes in a proscribed manner. The engine finishes by allowing the MD to post the note, which is then electronically signed and distributed, simultaneously to all key parties for a fee.
9. According to still other example embodiments, additional value items are associated with an operative note:
   1. tracking of surgical teaching;
   2. abilities and permanency track for worker's compensation;
   3. discharge summary data;
   4. follow-up data for specific procedures;
   5. ability to link multiple MD's together to study specific problems;
   6. ability to prospectively complete implant/device studies in a secure affordable manner; and
   7. Ability to collect CPT/surgeon/hospital specific case data and display against satisfaction data gleaned directly from patients contacted by the company acting as a neutral $3^{rd}$ party.

According to still other aspects of the invention, the methods and apparatus of the invention function simultaneously as a
   1. ASP for individual surgeons or health systems to accurately document surgical events.
   2. Portal for learning about surgery (Surgeon CME, patient)
   3. Interactive Web site for patients, providers, and purchasers of Operative services
   4. Business-to-Business pathway to monitor progress in treating a single patient, a group of patients with a single disease, or an entire population of patients. Patient's privacy can be built in to this system. However, particularly in work or vehicular injury cases, monitoring of the patients progress is common, although disorganized. This method would allow monitoring of therapy, prediction and calculation of disability, and comparison among groups (providers, patients, employers).
   5. Advertising Portal The method and apparatus of the invention can be accessed via the Intra/Internet. As an ASP for a practice it can offer direct access to case data at a lower cost for billing purposes than the current methods employed. Patients with "prescribed" access will see a postoperative care protocol designed for them by their provider. Patients without "prescribed" access can visit the generic portions of the site. Providers are encouraged to maintain their contacts with patients by participating in satisfaction surveys.

According to yet another example embodiment of the invention, the service provider hosting the on-line system owns "generic" case data derived from the patient data of physicians but stripped of any data identifying a particular patient. This ownership of the generic data is a term of the use of the system by a medical personnel. According to another embodiment, the individual physician can decide what parts of generic patient data, if any, to release for viewing. In this embodiment, a variety of users desire portions of the data owned by the service provider. Although individual patient case data will not be made available, data summaries are provided. In this scenario, the physician's case numbers would fall into a generic summary of the region. In this embodiment, the individual physician controls the individual physician's case data (for example, physician employees are managed as individuals with superimposed time-sensitive contracts. For example, it is envisioned that a physician who, after residency, joins a health maintenance organization or other group, will release all of her/his data to the organization for the period of her/his employment. Whatever her/his next job, the physician will no longer release procedure information to the organization. Questions will arise for individual physicians who work for large groups related to the volume of information that they are allowed to retain after leaving.

According to another example embodiment, large-scale data displays and research studies are currently desired. However, they are impossible to achieve because of the separate and unique nature of billing systems and interstate regulations. The method and apparatus of the present invention uses coding methods and descriptive language that is increasingly universal. In one example embodiment, codes used by the company are provided by the American Medical Association (AMA). A license fee is be paid by the system provider to the AMA for each registered customer. The company will cover this cost within a yearly registration fee charged to each physician customer. Because of it's large-scale, wide area deployment it is likely that its data can be used to understand medical problems and potential solutions. The present invention envisions variable charging for searches and studies. Examples of customers for searches are: medical insurers, Medicare, a large company which is partially self-insured, and a medical device manufacturer wanting to know the frequency of utilization of specific devices for specific diagnosis/treatments. Customers that request specific study designs could be: a group of specialists who seek to prove their excellence, a medical study group (the International Wrist Investigators), a medical Organization/Board (seeking to gain understanding of its own comparative skill against a competitive discipline (for example Family Physicians delivering babies compared to Ob/Gyn MD's).

According to still yet another example embodiment, highly targeted advertising is offered on the system pages to individuals about to "buy" a product. When patients access the system for informational purposes prior to a surgery or selecting a physician, the system reaches the patient/customer prior to use of their product inside the customer by the physician. Also, the system increases the efficiency of reaching targeted physicians by a medical device or other medical product, service or drug manufacturer. By suggesting/advertising products at the point in time that an operative event is planned, highly relevant information is placed in front of the physician at a highly effective time.

Thus, as described in more detail above, the present invention includes a number of features including:

1. X-Links
   Links/medical language operative terminology/cpt's/icd's/rvus in a manner visible to the MD
2. Geographic/Anatomic CPT Picker
   Presents data to MD in a manner familiar and allows selection of multiple cpts without constant renavigation
3. Geographic/Anatomic Results Display
   Allows MD to study personal practice without displaying results to world
4. Physician Picker
   Allow patients to see pattern of procedures as well as MD's willing to display results
5. Procedure Planning Templates
   Operative/Event planning tool which starts the process in office and alerts
   Or to equipment needs as well as allows MD to preplan case even completing the note the day before and review any latest equipment notes/care updates. This is a potential CME process.
6. Procedure documentation
   This portion of the process allows for one or many CPT codes to be combined into a single note, which matches the Hospitals, needs and can cross whatever EDI barrier exists. A key part of this process is its ability to cross into billing software for the MD and the hospital thus saving a labor step but not actually taking on the process of claims submission.
7. Custom procedure building
   Unlike some competitors, the content learns the users preferred method and defaults to the common screens. Also, the individual MD can modify the templates to be displayed to him/her without altering the main database.
8. Personal Data
   The MD can download and assemble data from his/her database without special programming skills. A report builder is provided.
9. Data is available following the principle of 5 9's. Data is permanent and private with shared overlapping ownership (patient, hospital, MD, insurer).

Figure 14:
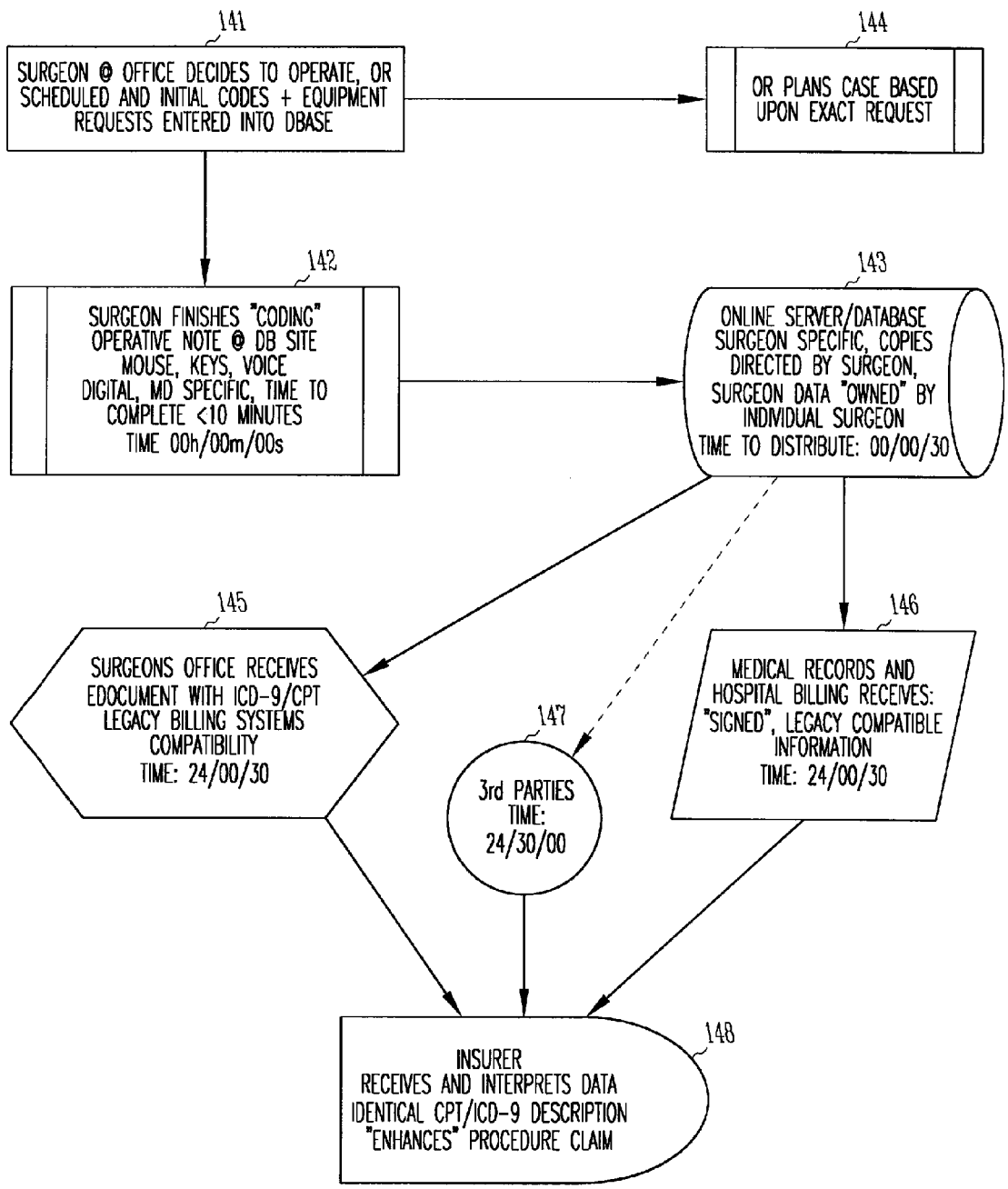
FIG. 14 illustrates an example embodiment of a data flow for planning an operative event, conducting it, and post event activities.

Referring now to FIG. 14, there is illustrated an example data flow for planning an operative event, conducting it, and post event activities. First, as illustrated in flow chart item 141, a surgeon decides to operate, the operating room (OR) is scheduled and the physician enters the initial planning codes and equipment into the online database. The surgeon finishes coding in the online database 142, and the data is then resident in the database 143. The OR can then receive this information from the online database and plan the surgery based upon an exact request 144. Once the surgery is complete, the final operative event data is entered into the database 143. The surgeon's office then receives an electronic document with the ICD9/CPT codes that are compatible with legacy billing systems, as shown in item 145. The medical records and hospital receives a electronically signed record of the operative event 146, and any third parties receive any desired information from the database 147. The insurer can subsequently receive the electronic records as illustrated in item 148. Due to the common origin of the operative event documentation from database 143, the ICD9 and CPT codes are identical and thus eliminates delays and inconsistencies that may detrimentally effect the reimbursement claim.

Additional Example Embodiment

According to one particular example embodiment, the wide area network of the invention is the Internet, and the on-line system is provided by a server on the Internet that supports client computers executing web browsers.

Figure 15B:
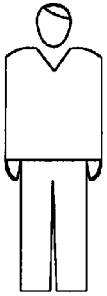

Referring now to FIGS. 15A-15J, there is illustrated a user interface (UI) according to one example embodiment of the invention. After identifying a patient, in this example patient Barbara B. Smith, the UI offers the physician or other health care professional user the choice to Pick CPT or Short Form Entry. If Pick CPT is chosen, the user is presented with the screen shown in FIG. 15B, allowing them to either select a region of the body from an image of the anatomy, in this case a skeletal image. Alternatively, a user may choose the CPT code directly from a drop down menu. If, for example, the user chooses the right forearm and wrist region (by pointing at it with a cursor controlled by a pointing device such as a mouse), the display of FIG. 15C is presented, showing a list of categories including, in this example, arthroscopy, casts, general, integrument, nerve and vascular. If the nerve category is selected, for example, the UI of FIG. 15D is presented, showing a list of subcategories including excision, neuroplasty, neurostim and repair. If the user chooses neuroplasty, the display of FIG. 15E is presented, with a list of CPT codes. If CPT code 64721 is selected, the display of FIG. 15F is presented, which requests the entry of event information including hospital, event date, medical record number, incisions start and incision close times, referring physicians, assistants, and assistants proficiency levels. At the bottom, the ICD9 codes that are cross referenced in the database to the chosen PCT code are displayed, and may be chosen by the physician by entering a check in the PreOp or PostOp boxes or both, indicating the ICD9 codes applicable before and after the surgery.

Referring to FIGS. 15G and H, there is illustrated a further event documentation input screen, including provision for a variety of procedure documentation including anesthesia, anesthesia class, unexpected events, estimated blood loss, preparations, drape, tournequet and tournequet time, equipment, and technique information, in this case incision type. Further, pathology can also be documented, including findings, In op testing and nerve, pathology comments. Discharge data, follow up timing, abilities data and notes can also be entered. If the documentation input meets the physician's approval, the post event data button is selected and the information is posted in to the on-line database. If not, the information can reset to its initial condition.

Figures 2, 15I:

FIG. 15I illustrates a discharge report that is generated after the documentation is posted, and includes itemization of procedure, preoperative and postoperative information, operative pathology and technique, as generated from the posted documentation. By pressing the discharge summary button, a discharge summary report is generated as shown in FIG. 15J, including procedure, discharge data and abilities information.

According to yet still another example embodiment, FIGS. 16A to 16C illustrate a cross reference table showing the cross referencing of CPT codes to ICD9 codes and other documentation entered by a physician or other input personnel, such as surgical techniques. Such techniques or preparation include, by way of example and not by limitation, tournequet, drape method and equipment lists cross-referenced to CPT codes.

Thus, as described above, the method and apparatus of the present invention solve many of the problems that the current system has, streamline the process, lower the costs and enter the market in a manner that yields immediate payback to the physicians. This web based system allows the physician to enter procedure information one time using simple, yet sophisticated screens that should allow the input of data in the same or less time as the physician currently takes to dictate the information. Partially, this input process is facilitated by providing a procedure notification screen for use by the physician's office-clinic which facilitates procedure planning for the office and hospital while at the same time reducing any keying requirements for the physician. At the end of a procedure, after the operative/event data is input, the physician can immediately review the information and send the completed information to both the hospitals systems and his systems at the same time. The system of the present invention also retains the information for later usage in licensing reports, patient satisfaction surveys and other value added solutions.

The consumer side to the system facilitates consumers searching for expert physicians with documented experience. This site is open to advertisers for the purpose of reaching patients with specific needs.

Thus, as described above, the present invention provides, in one or more of the embodiments described below, for a health care professional to build an original operative event note or documentation using a documentation database. In addition, at their option, change the content of a note or documentation online. Further, professionals may also, in some embodiments, add to the existing content of a documentation database within defined groups to better reflect their practice, without changing the structure to other users. Further, the manner in which the documentation database is presented to users can also be altered.

Thus, the approach of the various embodiments of the invention are designed to streamline an existing cost accountable step in the information gathering process, without trying to solve all of the problems in the medical information world. Physicians are already entering patient and procedure data utilizing changing, often cumbersome, phone based systems. The system seeks to simplify this process and increase the value of the data through effective capture techniques. The apparatus and method of the invention can immediately reduce physician and hospital overhead while increasing the quality of the information at the same time. An important side benefit is returning ownership of the operative record and lifetime work summary to the individual physician. In this age of rapid change, the value to the individual physician of a clear work record is large.

The invention claimed is:

1. A method, comprising:
a plurality of physicians who perform operative events and wherein each of the plurality of physicians has a subscription to an on-line system provided by an application service provider;
at least a first of the plurality of physicians performing different operative events at two or more different clinic or hospital organizations;
wherein the first physician enters operative event data for the different operative events into an operative event database, wherein the operative event data documents the different operative events;
the first physician entering the operative event data using a wide area network through a user interface assisting the first physician in coding operative events in a consistent manner at least in part by presenting for selection at least one pre-determined group of codes related to the operative event being coded;
the first physician accessing the operative event database to obtain information concerning the operative events entered by the first physician;
the application service provider maintaining the on-line system including one or more servers to support the entering of operative event data into the database through the wide area network and the user interface;

wherein the first physician can make the operative event data entered by the first physician available to only first selected ones of the plurality of clinic or hospital organizations;

at least one second physician entering operative event data respecting operative events performed by the second physician using the wide area network through the user interface assisting the second physician in coding operative events in a consistent manner by presenting for selection at least one pre-determined group of codes related to the operative event being coded;

wherein a second physician can make the operative event data entered by the second physician available to only second selected ones of the plurality of clinic or hospital organizations the second physician allows to access the operative event data entered by the second physician;

each of the plurality of physicians paying at least one charge to the application service provider for use of the on-line system to document operative events and to distribute operative event data to the plurality of clinic or hospital organizations;

wherein the plurality of physicians retain control over the use and disposition of the operative event data entered by the physicians;

entering at least some patient outcome data for operative events wherein the outcome data is correlated with at least some of the coded operative events entered by the plurality of physicians, and wherein the application service provider maintains the integrity of the patient outcome data; and making at least some of the operative event data and associated outcome data for at least some of the plurality of physicians available to at least some other parties.

2. A method according to claim 1 wherein an assistant enters the operative event data for the physician.

3. A method according to claim 1 further wherein the operative event data is used to obtain payment from a payer for medical services rendered.

4. A method according to claim 1 further wherein more than one physician uses the system to enter coding for different medical services rendered in connection with the same operative event.

5. A method according to claim 4 further wherein the system assists in conforming one of the codings for an operative event with another coding for the same operative event.

6. A method according to claim 1 further wherein at least some of the operative event data is made available to third parties.

7. A method according to claim 6 further wherein the operative event data is made available so that any patient identifying information is omitted.

8. A method according to claim 6 wherein the operative event data is made available in summary form.

9. A method according to claim 6 wherein the operative event data is made available according to geographical areas.

10. A method according to claim 1 further including making operative event data for a subscriber physician available to potential patients.

11. A method according to claim 10 further including entering patient outcome data into the system and correlating the outcome data with coded operative events.

12. A method according to claim 11 further including making at least (i) a summary of operative event data or (ii) outcomes associated with operative events for a subscriber physician available to potential patients.

13. A method according to claim 1 including reporting coded operative events by frequency of diagnosis, procedure, age distribution, and satisfaction index.

14. A method according to claim 1 including reporting coded operative events to a physician office, hospital or designated copy sites for use or distribution.

15. A method according to claim 14 including combining reporting coded operative events for a plurality of physicians to form a group report.

16. A method according to claim 15 including comparing an individual physician's coded operative events summary with a group summary.

17. A method according to claim 1 further including collecting similar coded operative events for different patients and associated outcomes as part of a study and reporting the collected data to allow tracking of a study.

18. A method according to claim 1 further including inputting patient satisfaction data into the system corresponding to operative events.

19. A method according to claim 18 further including reporting patient satisfaction data.

20. A method according to claim 19 above wherein the reporting is obtained on-line by a prospective patient.

21. A method according to claim 1 further including the physician electronically signing the operative event data.

22. A method according to claim 1 further including a physician paying a fee to the service provider based on the entry of an operative note into the system.

23. A method according to claim 1 further including downloading an operative note to a hospital and the hospital paying a fee to the service provider for downloading an operative note.

24. A method according to claim 1 further including generating discharge reports from the system in response at least in part to the operative event data entered by physicians.

25. A method according to claim 24 further including a hospital or clinic treating a discharged patient paying the service provider a fee for each discharge report.

26. A method according to claim 1 further including a physician paying the service provider an annual charge for access to the system.

27. A method according to claim 1 further including a non-physician entity paying an annual fee for access to the system.

28. A method according to claim 1 further including outputting printed reports, electronic reports or electronic downloads of operative event data from the system.

29. A method according to claim 1 further including allowing the code entering physician to view and access his or her data only.

30. A system, comprising:

an on-line system including one or more servers to support the entering of operative event data into an operative event database through a wide area network and a user interface presented on a client computer, wherein the on-line system is an application service provider system;

the operative event database containing operative event data documenting completed operative events performed by a plurality of physicians who perform operative events and wherein each of the plurality of physicians has a subscription to the on-line system and at least a first of the plurality of physicians performs different operative events at two or more different clinic or hospital organizations and at least a second of the plurality of physicians performs other operative events at the same or other of the two or more different clinic or hospital organizations;

the client computer connected to the one or more servers through a wide area network;

the user interface adapted to assist the first physician in coding operative events in a consistent manner at least in part by presenting for selection at least one pre-determined group of codes related to the operative event being coded;

wherein the first physician enters operative event data for the different operative events into the operative event database, wherein the operative event data documents the different operative events;

an account management system operative on the one or more servers and maintaining a list of subscribing physicians authorized to use the on-line system;

a billing module operative on the one or more servers to charge each of the plurality of physicians at least one charge payable to the application service provider for use of the on-line system to document operative events and to distribute operative event data from the on-line system to the plurality of clinic or hospital organizations;

an operative event data management system operative on the one or more servers allowing authorized physicians to control the use and disposition of the operative event data entered by the physician in the on-line system;

wherein the operative event data management system is further operative on the one or more servers to enable the first physician or the second physician to make the operative event data entered by the respective first physician or second physician available to only respective first selected ones or second selected ones of the plurality of clinic or hospital organizations;

a data input module to enter at least some patient outcome data for operative events and to correlate the outcome with at least some of the coded operative events entered by the plurality of physicians, and wherein the application service provider maintains the integrity of the patient outcome data; and a data output module to make at least some of the operative event data and associated outcome data for at least some of the plurality of physicians available to at least some other parties.

31. A system according to claim 30 wherein an assistant enters the operative event data for the physician.

32. A system according to claim 30 further wherein the operative event data is used to obtain payment from a payer for medical services rendered.

33. A system according to claim 30 further wherein the operative event data is entered by more than one physician to document different medical services rendered in connection with the same operative event.

34. A system according to claim 33 further wherein the system includes a data processing module that assists in conforming one of the codings for an operative event with another coding for the same operative event.

35. A system according to claim 30 further including a data output module outputting at least some of the operative event data to third parties.

36. A system according to claim 35 further wherein the operative event data is output without any patient identifying information.

37. A system according to claim 35 wherein the operative event data is output in summary form.

38. A system according to claim 35 wherein the operative event data is output according to geographical areas.

39. A system according to claim 30 further including a prospective patient data output module for making operative event data for a subscriber physician available to potential patients.

40. A system according to claim 39 further including an outcome data input and storage system for entering patient outcome data into the system and correlating the outcome data with coded operative events.

41. A system according to claim 40 further including a reporting module for making at least a summary of operative event data and associated outcomes for a subscriber physician available to potential patients.

42. A system according to claim 30 including a further reporting module for reporting coded operative events by frequency of diagnosis, procedure, age distribution, and satisfaction index.

43. A system according to claim 30 including a reporting module for outputting coded operative event reports to a physician office, hospital or designated copy sites for use or distribution.

44. A system according to claim 43 further wherein the reporting module includes a sub-module for combining reporting coded operative events for a plurality of physicians to form a group report.

45. A system according to claim 44 further wherein the reporting module includes a sub-module for comparing an individual physician's coded operative events summary with a group summary.

46. A system according to claim 30 further a study module for collecting similar coded operative events for different patients and associated outcomes as part of a study and reporting the collected data to allow tracking of a study.

47. A system according to claim 30 further including a satisfaction data input module receiving patient satisfaction data into the system corresponding to operative events.

48. A system according to claim 47 further including a satisfaction data output module.

49. A system according to claim 30 further including a signing module enabling a physician to electronically sign the operative event data.

50. A system according to claim 30 further including a billing module for charging a physician a fee to the service provider based on the entry of an operative note into the system.

51. A system according to claim 30 further wherein the billing module includes a sub-module for charging a fee to a hospital for downloading an operative note.

52. A system according to claim 30 further including a discharge reporting module for generating discharge reports from the system in response at least in part to the operative event data entered by physicians.

53. A system according to claim 52 further wherein the billing module includes a sub-module for billing a hospital or clinic treating a discharged patient a fee for each discharge report.

54. A system according to claim 30 further wherein the billing module includes a sub-module for charging a physician or other entity an annual charge for access to the system.

55. A system according to claim 30 further including an output sub-module for outputting printed reports, electronic reports or electronic downloads of operative event data from the system.

56. A system according to claim 30 further including a sub-module allowing the code entering physician to view and access his or her data only.

* * * * *